(12) United States Patent
Genta et al.

(10) Patent No.: US 9,404,135 B2
(45) Date of Patent: Aug. 2, 2016

(54) BIOMASS DECOMPOSITION APPARATUS AND METHOD THEREOF, AND SUGAR-SOLUTION PRODUCTION SYSTEM USING BIOMASS MATERIAL

(75) Inventors: Minoru Genta, Tokyo (JP); Seiichi Terakura, Tokyo (JP); Yasushi Kageyama, Tokyo (JP); Ryosuke Uehara, Tokyo (JP); Seiji Kobayashi, Tokyo (JP)

(73) Assignee: MITSUBISHI HEAVY INDUSTRIES MECHATRONICS SYSTEMS, LTD., Kobe (JP)

( * ) Notice: Subject to any disclaimer, the term of this patent is extended or adjusted under 35 U.S.C. 154(b) by 0 days.

(21) Appl. No.: 13/121,969

(22) PCT Filed: Sep. 3, 2010

(86) PCT No.: PCT/JP2010/065175
§ 371 (c)(1),
(2), (4) Date: Mar. 31, 2011

(87) PCT Pub. No.: WO2012/029182
PCT Pub. Date: Mar. 8, 2012

(65) Prior Publication Data
US 2012/0058544 A1  Mar. 8, 2012

(51) Int. Cl.
*C02F 3/34* (2006.01)
*C12P 1/00* (2006.01)
(Continued)

(52) U.S. Cl.
CPC . *C12P 19/14* (2013.01); *B08B 1/04* (2013.01); *B08B 9/00* (2013.01); *C10L 1/02* (2013.01);
(Continued)

(58) Field of Classification Search
CPC ............. B08B 1/04; C10L 1/02; C10L 9/086;
C10L 5/44; C12P 19/14; C13K 1/02; C10G 2300/1011; C10G 2300/1014; Y02E 50/10; Y02E 50/16; Y02E 50/30
USPC ........ 435/262, 290.4; 422/258, 261; 366/133, 366/156.1, 158.5, 164.4
See application file for complete search history.

(56) References Cited

U.S. PATENT DOCUMENTS 3,985,728 A   10/1976  Lin
4,023,982 A   5/1977   Knauth
(Continued)

FOREIGN PATENT DOCUMENTS

CA  2660990 A1  8/2009
CA  2666152 A1  4/2010
(Continued)

OTHER PUBLICATIONS

"Biomass Ethanol"; Nikkei Biotechnology & Business, Sep. 2002, Nikkei Business Publications Inc, pp. 52-61. (w/partial English translation).
(Continued)

*Primary Examiner* — Michael Hobbs
(74) *Attorney, Agent, or Firm* — Westerman, Hattori, Daniels & Adrian, LLP

(57) ABSTRACT

To include a hydrothermal decomposition unit that transports a fed biomass material from one side (a lower side) to the other side (an upper side) by a screw 14 in an apparatus body, feeds pressurized hot water, hydrothermally decomposes the biomass material, transfers hot-water soluble fractions into a hot-water effluent and separates a lignin component and a hemicellulose component from the biomass material, and also to include a biomass discharging unit. Further, a scraping unit is provided at an end of a flight of the screw positioned within an installation area of the solid-liquid separator.

17 Claims, 12 Drawing Sheets

(51) Int. Cl.

| | | |
|---|---|---|
| *C12P 19/14* | (2006.01) | |
| *B08B 1/04* | (2006.01) | |
| *B08B 9/00* | (2006.01) | |
| *C10L 1/02* | (2006.01) | |
| *C10L 5/44* | (2006.01) | |
| *C10L 9/08* | (2006.01) | |
| *C13K 1/02* | (2006.01) | |

(52) U.S. Cl.
CPC . *C10L 5/44* (2013.01); *C10L 9/086* (2013.01); *C13K 1/02* (2013.01); *C10G 2300/1011* (2013.01); *C10G 2300/1014* (2013.01); *C12P 2201/00* (2013.01); *Y02E 50/10* (2013.01); *Y02E 50/16* (2013.01); *Y02E 50/30* (2013.01); *Y02P 30/20* (2015.11)

(56) References Cited

U.S. PATENT DOCUMENTS

| | | | |
|---|---|---|---|
| 4,152,197 A | 5/1979 | Lindahl et al. | |
| 4,650,689 A | 3/1987 | Hedrick | |
| 4,746,401 A | 5/1988 | Roberts et al. | |
| 4,779,186 A * | 10/1988 | Handke et al. | 700/67 |
| 4,859,322 A * | 8/1989 | Huber | 210/162 |
| 5,348,871 A | 9/1994 | Scott et al. | |
| 5,411,594 A | 5/1995 | Brelsford | |
| 5,424,417 A | 6/1995 | Torget et al. | |
| 5,466,108 A | 11/1995 | Piroska | |
| 5,891,433 A * | 4/1999 | Silver | 424/123 |
| 6,022,419 A | 2/2000 | Torget et al. | |
| 6,419,788 B1 | 7/2002 | Wingerson | |
| 6,461,523 B1 * | 10/2002 | Greenrose | 210/770 |
| 8,123,864 B2 | 2/2012 | Christensen et al. | |
| 8,163,517 B2 | 4/2012 | Genta et al. | |
| 2002/0148575 A1* | 10/2002 | Wingerson | 162/14 |
| 2004/0002028 A1* | 1/2004 | Smith | 431/1 |
| 2007/0231869 A1 | 10/2007 | Holmgren et al. | |
| 2007/0259412 A1 | 11/2007 | Belanger et al. | |
| 2008/0026431 A1 | 1/2008 | Saito et al. | |
| 2008/0032344 A1 | 2/2008 | Fallavollita | |
| 2008/0044891 A1 | 2/2008 | Kinley et al. | |
| 2008/0299628 A1 | 12/2008 | Hallberg et al. | |
| 2010/0108567 A1 | 5/2010 | Medoff | |
| 2010/0184176 A1 | 7/2010 | Ishida et al. | |
| 2010/0269990 A1 | 10/2010 | Dottori et al. | |
| 2010/0285574 A1 | 11/2010 | Genta et al. | |
| 2010/0330638 A1 | 12/2010 | Aita et al. | |
| 2011/0003348 A1 | 1/2011 | Genta et al. | |
| 2011/0079219 A1 | 4/2011 | McDonald et al. | |
| 2011/0314726 A1 | 12/2011 | Jameel et al. | |
| 2012/0006320 A1 | 1/2012 | Nguyen | |
| 2012/0315683 A1 | 12/2012 | Mosier et al. | |
| 2014/0004571 A1 | 1/2014 | Garrett et al. | |
| 2014/0273127 A1 | 9/2014 | Fuchs et al. | |

FOREIGN PATENT DOCUMENTS

| | | |
|---|---|---|
| CA | 2750754 A1 | 1/2012 |
| CA | 2654306 C | 10/2013 |
| EP | 0 098 490 A2 | 1/1984 |
| JP | 9-507386 A | 7/1997 |
| JP | 11-506934 A | 6/1999 |
| JP | 2001-170601 A | 6/2001 |
| JP | 2002-059118 A | 2/2002 |
| JP | 2003-311141 A | 11/2003 |
| JP | 2004-105855 A | 4/2004 |
| JP | 2005-027541 A | 2/2005 |
| JP | 2005-168335 A | 6/2005 |
| JP | 2005-205252 A | 8/2005 |
| JP | 2005-229821 A | 9/2005 |
| JP | 2006-036977 A | 2/2006 |
| JP | 2006-136263 A | 6/2006 |
| JP | 2006-223152 A | 8/2006 |
| JP | 2006-289164 A | 10/2006 |
| JP | 2007-112880 A | 5/2007 |
| JP | 2007-202560 A | 8/2007 |
| JP | 2007-301472 A | 11/2007 |
| JP | 2008-054608 A | 3/2008 |
| JP | 2008-104452 A | 5/2008 |
| JP | 2008-278825 A | 11/2008 |
| JP | 2009-183153 A | 8/2009 |
| JP | 2009-183154 A | 8/2009 |
| JP | 2009-183805 A | 8/2009 |
| JP | 2010-17084 A | 1/2010 |
| JP | 4764527 B1 | 9/2011 |
| JP | 4764528 B1 | 9/2011 |
| WO | 84/03304 A1 | 8/1984 |
| WO | 95/17517 A1 | 6/1995 |
| WO | 96/40970 A1 | 12/1996 |
| WO | 2009/096061 A1 | 6/2009 |
| WO | 2009/096060 A1 | 8/2009 |
| WO | 2009/096062 A1 | 8/2009 |
| WO | 2009/124240 A1 | 10/2009 |
| WO | 2010/038302 A1 | 4/2010 |
| WO | 2013/082616 A2 | 6/2013 |

OTHER PUBLICATIONS

International Search Report of PCT/JP2010/065175, date of mailing Sep. 3, 2010.

Written Opinion of the International Searching Authority of PCT/JP2010/065175, date of mailing Nov. 1, 2010.

English machine translation of JP2007-301472 (JP 2007-301472 filed Mar. 31, 2011) in Non-Final Office Action dated Mar. 11, 2013 issued in U.S. Appl. No. 12/443,515.

Genta, "NEDO ni yoru Biomass Energy to Ko Koritsu Tenkan Gijutsu Kaihatsu 1), Suinetsu Bunkaiho to Koso Bunkaiho wo Kumiawaseta Nogyo Zansa to no Cellulose-kei Biomass no Tei Cost Toka Gijutsu no Kaihatsu" Clean Energy, 2010, pp. 11-15, in the Australian Notice of Acceptance dated Mar. 17, 2014, on Apr. 30, 2014.

Canadian Office Action dated Mar. 31, 2014, issued in Canadian Patent Application No. 2,750,753 (3 pages) (corresponding to U.S. Appl. No. 13/203,929).

U.S. Final Office Action dated May 22, 2014, issued in U.S. Appl. No. 13/700,753 (40 pages).

U.S. Final Office Action dated Jun. 3, 2014, issued in U.S. Appl. No. 13/203,929 (22 pages).

U.S. Final Office Action dated Jul. 3, 2014, issued in U.S. Appl. No. 13/578,116 (17 pages).

U.S. Final Office Action dated Aug. 18, 2014, issued in U.S. Appl. No. 13/132,034 (30 pages).

U.S. Final Office Action dated Jun. 13, 2014, issued in U.S. Appl. No. 12/438,792 (26 pages).

U.S. Non-Final Office Action dated Aug. 27, 2014, issued in U.S. Appl. No. 13/132,040 (53 pages).

U.S. Final Office Action dated Jul. 22, 2014, issued in U.S. Appl. No. 12/443,515 (13 pages).

Arroyo-Lopez, F.N. et al., "Effects of temperature, pH and sugar concentration on the growth parameters of *Saccharomyces cerevisiae*, *S. kudriavzevii* and their interspecific hybrid", International Journal of Food Microbiology, vol. 131, pp. 120-127 (2009).

Turton, L.J. et al., "Effect of Glucose Concentration in the Growth Medium Upon Neutral and Acidic Fermentation End-products of Clostridium Bifermentans, Clostridium Sporogenes and Peptostreptococcus Anaerobius", J. Med. Microbiol., vol. 16, pp. 61-67 (1983).

Dien, B.S. et al., "Fermentation of hexose and pentose sugars using a novel ethanologenic *Escherichia coli* strain", Enzyme and Microbial Technology, vol. 23, pp. 366-371 (1998).

U.S. Office Action dated Aug. 19, 2013, issued in U.S. Appl. No. 13/578,116.

U.S. Office Action dated Oct. 3, 2013, issued in U.S. Appl. No. 13/782,545.

English translation of JP 2009-183805 previously filed on Mar. 31, 2011, in U.S. Office Action U.S. Appl. No. 13/782,545.

Canadian Notice of Allowance dated Aug. 22, 2013, issued in Canadian Patent Application No. 2666152.

(56) References Cited

OTHER PUBLICATIONS

Canadian Notice of Allowance dated Aug. 22, 2013, issued in Canadian Patent Application No. 2713529.
U.S. Office Action dated Oct. 28, 2013, issued in U.S. Appl. No. 12/443,515.
U.S. Office Action dated Oct. 7, 2013, issued in U.S. Appl. No. 13/700,753.
U.S. Restriction/Elections dated Aug. 22, 2013, issued in U.S. Appl. No. 13/700,753.
Canadian Office Action dated Nov. 8, 2013, issued in Canadian Patent Application No. 2,801,383 (2 pages).
Indonesian Notice of Allowance dated Nov. 15, 2013, issued in Indonesian Patent Application No. W-00201002623, w/English translation, (5 pages).
Canadian Notice of Allowance dated Jan. 13, 2014, issued in Canadian Patent Application No. 2,744,522 (1 page).
U.S. Non-Final Office Action dated Dec. 16, 2013, issued in U.S. Appl. No. 13/132,034 (29 pages).
U.S. Non-Final Office Action dated Dec. 17, 2013, issued in U.S. Appl. No. 13/203,929 (23 pages).
U.S. Non-Final Office Action dated Jan. 30, 2014 issued in U.S. Appl. No. 12/438,792 (39 pages).
U.S. Non-Final Office Action dated Jan. 30, 2014, issued in U.S. Appl. No. 13/578,116 (22 pages).
Gregg, D. et al., "Bioconversion of Lignocellulosic Residue to Ethanol: Process Flowsheet Development", Biomass and Bioenergy, 1995, vol. 9, No. 1-5, pp. 287-302, in U.S. Office Action dated Dec. 17, 2013.
Kumagai Satoshi et al. "Fractionation and Saccharification of Cellulose and Hemicellulose in Rice Hull by Hot-Compressed-Water Treatment with Two-Step Heating", Journal of the Japan Institute of Energy, Dec. 1, 2004, vol. 83, pp. 776-781, in Notice of Acceptance dated Mar. 4, 2014, issued in Japanese Patent Application No. 2009-252201.
US Final Office Action dated Feb. 13, 2014, issued in U.S. Appl. No. 12/865,273 (26 pages).
Liu, Chaogang, et al., "Continuous Fermentation of Hemicellulose Sugars and Cellulose to Ethanol", International Symposia on Alcohol Fuels, (2005), pp. 1-28 (in U.S. Final Office Action dated Feb. 13, 2014, issued in U.S. Appl. No. 12/865,273).
U.S. Non-Final Office Action issued Mar. 10, 2014, in related U.S. Appl. No. 13/782,545 (27 pages).
Decision of a Patent Grant dated Mar. 4, 2014, issued in JP2009-252201 (corresponds to U.S. Appl. No. 12/443,515), w/English translation (4 pages).
Decision of a Patent Grant dated Mar. 4, 2014, issued in JP2009-245963 (corresponds to U.S. Appl. No. 12/438,792) w/English translation (4 pages).
Australian Notice of Acceptance dated Mar. 17, 2014, issued in Australian patent application No. 2011355013 (corresponding to U.S. Appl. No. 13/578,116), (2 pages).
U.S. Office Action dated Apr. 14, 2014, issued in U.S. Appl. No. 12/443,515 (16 pages).
Office Action dated Nov. 14, 2014, issued in corresponding Indonesian Patent Application No. W00201102352, w/English translation.
Office Action dated Nov. 7, 2014, issued in Indonesian Patent Application No. W00200902414, (corresponds to U.S. Appl. No. 12/438,792), w/English translation.
Genda, M. et al., "Suinetsu Bunkaiho To Koso Bunkaiho o Kumiawaseta Nogyo Zansa To no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF_00003.html, in JP Office Action dated Oct. 14, 2014.
Lehrburger, E. "Developing biorefineries to produce energy, ethanol and other industrial products", PureVision Technology, Inc., Alternative Energy Conference, Mar. 3, 2015, pp. 1-26, in U.S. Office Action dated Nov. 6, 2014.

U.S. Office Action dated Sep. 30, 2014, issued in U.S. Appl. No. 13/782,545 (43 pages).
U.S. Office Action dated Nov. 6, 2014, issued in U.S. Appl. No. 12/865,273 (27 pages).
Japanese Office Action dated Oct. 14, 2014, issued in Japanese Patent Application No. 2010-154233 (corresponds to U.S. Appl. No. 13/700,753), with English Translation (7 pages).
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
U.S. Office Action dated Dec. 26, 2014, issued in U.S. Appl. No. 13/132,040.
Non-Final Office Action dated Jun. 19, 2015, issued in U.S. Appl. No. 13/700,753 (34 pages).
Final Office Action dated Aug. 6, 2015, issued in U.S. Appl. No. 14/381,511 (14 pages).
Notice of Allowance dated Aug. 19, 2015, issued in U.S. Appl. No. 12/438,792 (12 pages).
Notice of Allowance dated Aug. 12, 2015, issued in U.S. Appl. No. 13/578,116 (48 pages).
Non-Final Office Action dated Aug. 21, 2015, issued in U.S. Appl. No. 13/203,929 (18 pages).
Notice of Allowance dated Jul. 6, 2015, issued in Indonesian application No. W-002011035222 (counterpart of U.S. Appl. No. 13/203,929), with English translation (4 pages).
International Search Report dated Jul. 3, 2012 issued in International Application No. PCT/JP2012/058460 (corresponds to U.S. Appl. No. 14/381,511).
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/English translation (corresponds to U.S. Appl. No. 14/381,511) (4 pages).
U.S. Office Action dated Apr. 24, 2015, issued in U.S. Appl. No. 14/381,511 (20 pages).
Notice of Allowance and Fee(s) Due dated Feb. 17, 2015, issued in U.S. Appl. No. 13/782,545 (20 pages).
U.S. Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).
U.S. Office Action dated Mar. 31, 2015, issued in U.S. Appl. No. 12/865,273 (25 pages).
U.S. Office Action dated May 13, 2015, issued in U.S. Appl. No. 12/438,792 (11 pages).
Decision of a Patent Grant dated Nov. 10, 2015 issued in Japan application No. 2010-154233 (counterpart to U.S. Appl. No. 13/700,753); (5 pages); with English translation.
Office Action dated Sep. 28, 2015, issued in U.S. Appl. No. 13/203,848 (34 pages).
Notice of Allowance dated Sep. 30, 2015, issued in CA 2,791,665 (counterpart to U.S. Appl. No. 13/578,116).
Office Action dated Jul. 10, 2015 (received from Australian Patent Office on Oct. 13, 2015), issued in AU 2012374915 (counterpart to U.S. Appl. No. 14/381,511).
Notice of Allowance dated May 5, 2016, issued in U.S. Appl. No. 13/203,848, (23 pages).
Notice of Allowance dated Mar. 30, 2016, issued in Indonesian Application No. W-00200902414(counterpart to U.S. Appl. No. 12/438,792), with English translation (4 pages).
Notification of Result of Substantive Examination dated Mar. 30, 2016, issued in Indonesian Patent Application No. W-00201102351(counterpart to U.S. Appl. No. 13/132,034), with English translation. (4 pages).

* cited by examiner

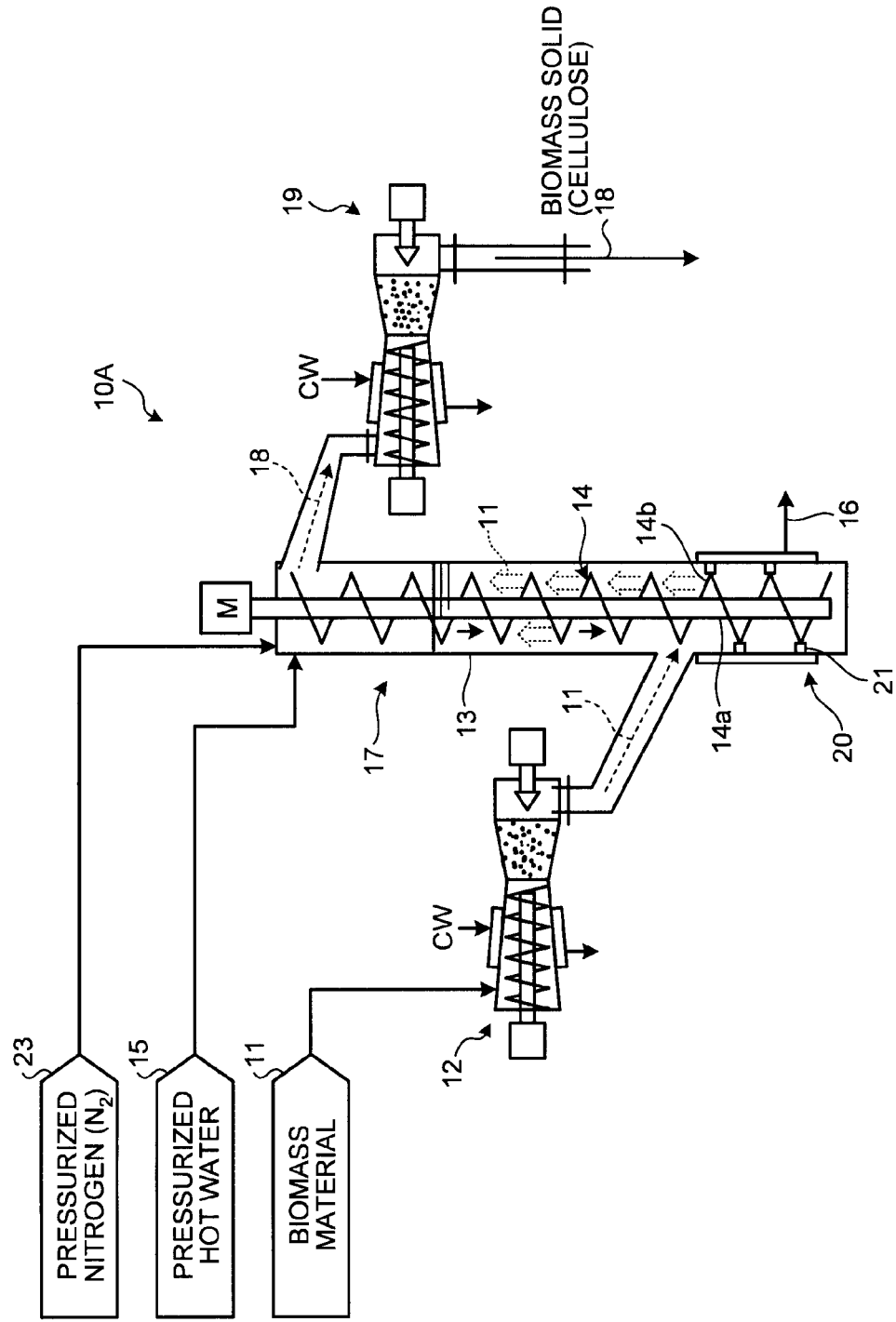

BIOMASS DECOMPOSITION APPARATUS AND METHOD THEREOF, AND SUGAR-SOLUTION PRODUCTION SYSTEM USING BIOMASS MATERIAL

FIELD

The present invention relates to a biomass decomposition apparatus that can decompose a biomass material and efficiently perform solid-liquid separation into a biomass solid and a water soluble, a method thereof, and a sugar-solution production system that uses a biomass material and can efficiently produce an organic raw material such as alcohol, substitutes for petroleum, or amino acid, the sugar-solution production system using the biomass decomposition apparatus and the method thereof.

BACKGROUND

Conventionally, a technique for producing ethanol or the like, in which solid-liquid separation is performed after saccharification of biomass such as wood by using diluted sulfuric acid or concentrated sulfuric acid, and a liquid phase is neutralized and used as a raw material for ethanol fermentation, has been practical utilized (Patent Literature 1, Patent Literature 2).

Further, production of chemical industrial raw materials (for example, lactic acid fermentation) using sugar as a starting material can be also considered.

In this specification, "biomass" represents organisms incorporated in a substance circulatory system of the global biosphere or accumulation of organic matters derived from the organisms (see JIS K 3600 1258).

Sugarcane, corn and the like, which are currently used as alcohol raw materials, are originally used as food and using these edible resources as industrial resources in a long term and in a stable manner is not preferable in view of a life cycle of effective foodstuff.

Therefore, it is an important issue to effectively use cellulose resources such as herbal biomass and wood-based biomass, which are believed to be useful industrial recourses in the future.

Further, in the cellulose resources, the resource component ratio is varied such that the ratio of cellulose is 38% to 50%, that of hemicellulose component is 23% to 32%, and that of lignin component, which is not used as a fermentation raw material, is 15% to 22%. Because industrial researches have been conducted with many unsolved problems, raw materials in the researches are assumed in a fixed manner, and currently there is no disclosure of a technique of a production system with taking the material versatility of into consideration.

Originally, because issues of waste and prevention of the global warming are taken into consideration according to a method unfavorable to fermentation feedstock as compared with starch feedstock, there is less point in the production system in which raw materials are considered in a fixed manner. This production system should be widely applicable to general waste materials. Enzymic saccharification itself is not efficient at all, and is thought to be an issue that should be solved in the future. A saccharification rate by acid treatment has a considerably small value of about 75% (on a component basis capable of being saccharified) due to excessive decomposition of sugar caused by overreaction. Therefore, the production yield of ethanol is about 25% with respect to the cellulose resources (Patent Literature 1, Patent Literature 3).

In the conventional techniques disclosed in Patent Literatures 1 to 3, there has been a phenomenon in which a reaction by-product causes inhibition of enzymic saccharification to decrease the sugar yield. Therefore, a hydrothermal decomposition apparatus that removes a substance inhibiting enzymic saccharification to increase activity of enzyme based on cellulose has been proposed (Patent Literatures 4 and 5).

CITATION LIST

Patent Literatures

Patent Literature 1: Japanese Patent Application National Publication No. H9-507386
Patent Literature 2: Japanese Patent Application National Publication No. H11-506934
Patent Literature 3: Japanese Patent Application Laid-open No. 2005-168335
Patent Literature 4: Japanese Patent Application Laid-open No. 2009-183805
Patent Literature 5: Japanese Patent Application Laid-open No. 2009-183154

Non Patent Literature

Non Patent Literature 1: Nikkei Bio Business, p. 52, September 2002

SUMMARY

Technical Problem

In the hydrothermal decomposition apparatus in Patent Literatures 4 and 5 mentioned above, a biomass solid and pressurized hot water are fed into counter contact with each other to cause hydrothermal reaction by internal heat exchange. However, when pressurized hot water is discharged, there is a problem that the biomass solid becomes blockage at the time of discharging the hot water, and efficient solid-liquid separation cannot be performed.

Therefore, it can be considered that an effluent after a decomposing process is discharged to outside in a state of solid-liquid mixed phase together with the biomass solid, and a solid-liquid separation device such as a belt filter is provided outside of the apparatus to perform solid-liquid separation, so that a solid content is carried to the decomposition apparatus again and a liquid content is carried to a post-processing system. However, because the solid-liquid separation device is separately provided outside, the cost of the apparatus increases and an installation space is required. Further, when solid-liquid separation is performed outside, a dissolved hemicellulose component precipitates on a hot water side, and as a result, the recovery efficiency of hot water soluble is reduced.

The present invention has been achieved to solve the above problems, and an object of the present invention is to provide a biomass decomposition apparatus that can efficiently perform solid-liquid separation into a biomass solid and a water soluble and a method thereof, and a sugar-solution production system using a biomass material.

Solution to Problem

According to an aspect of the present invention, a biomass decomposition apparatus that decomposes a biomass material containing cellulose, hemicellulose, and lignin, the apparatus includes: a biomass feeding unit that feeds a biomass material; a decomposition unit that transports a fed biomass material from one side to the other side by a screw inside an apparatus body, feeds treat water from the other side, which is different from a feed position of the biomass material, into the apparatus body, decomposes the biomass material while bringing the biomass material into counter contact with treat water, transfers soluble fractions into an effluent, which is treat water to be discharged, and separates a lignin component and a hemicellulose component from the biomass material; a biomass discharging unit that discharges a biomass solid from the other side of the apparatus body; and a solid-liquid separator that discharges an effluent from one side of the apparatus body. A scraping unit is provided at an end of a flight of the screw positioned within an installation area of the solid-liquid separator.

Advantageously, in the biomass decomposition apparatus, the scraping unit abuts against a surface of the solid-liquid separator.

Advantageously, in the biomass decomposition apparatus, the scraping unit is provided at a plurality of positions over an entire circumference of a flight.

Advantageously, in the biomass decomposition apparatus, the scraping unit has a brush shape formed by bundling wires.

Advantageously, in the biomass decomposition apparatus, the solid-liquid separator is a filter.

Advantageously, in the biomass decomposition apparatus, each one of the wires has a wire diameter insertable into a gap between filters in the solid-liquid separator.

Advantageously, in the biomass decomposition apparatus, each one of the wires is formed of a twisted wire formed by twisting thin wires.

Advantageously, in the biomass decomposition apparatus, the solid-liquid separator is formed over an entire circumference of an apparatus body.

Advantageously, in the biomass decomposition apparatus, an aperture shape of a filter in the solid-liquid separator expands from an inlet side toward an outlet side.

Advantageously, in the biomass decomposition apparatus, a heat exchanger is provided in a discharge line of the effluent.

Advantageously, in the biomass decomposition apparatus, water that has been heat-exchanged by the heat exchanger is pressurized and heated to obtain pressurized hot water by a pressurizing and heating unit, and a pressurized hot-water line for feeding pressurized hot water to the decomposition apparatus is provided.

Advantageously, in the biomass decomposition apparatus, a flowmeter is provided in a discharge line of the effluent, and a controller controls a flow rate so that an discharge flow rate becomes constant.

According to another aspect of the present invention, a biomass decomposition method includes: feeding a biomass material containing cellulose, hemicellulose, and lignin; decomposing the biomass material with treat water in a decomposition unit; dissolving a lignin component and a hemicellulose component in the treat water; and thereafter, separating a solid content accumulated in a solid-liquid separator into solid and liquid by scraping off a solid content by a scraping unit provided at an end of a flight of a screw, when an effluent is discharged from the decomposition unit.

According to still another aspect of the present invention, a sugar-solution production system using a biomass material includes: any one of the above described biomass decomposition apparatus; and an enzymatic decomposition device that processes at least one of cellulose in a biomass solid discharged from the biomass decomposition apparatus and a hemicellulose component in an effluent with enzyme into a sugar solution containing at least one of hexose and pentose.

Advantageously, in the sugar-solution production system using a biomass material includes a sulfuric-acid decomposition device that decomposes the hemicellulose component in the effluent discharged from the biomass decomposition apparatus with sulfuric acid into a sugar solution containing pentose.

Advantageous Effects of Invention

According to the present invention, a solid content accumulated in a solid-liquid separator is scraped off by a scraping unit provided at an end of a flight of a screw to prevent blockage. Further, the removed solid content is lifted due to a transporting function of the flight, and as a result, the solid content is used as a material for counter contact, thereby promoting efficient decomposition.

BRIEF DESCRIPTION OF DRAWINGS

FIG. 1 is a schematic diagram of a biomass hydrothermal decomposition apparatus according to a first embodiment of the present invention.

DESCRIPTION OF EMBODIMENTS

Figure 2A:
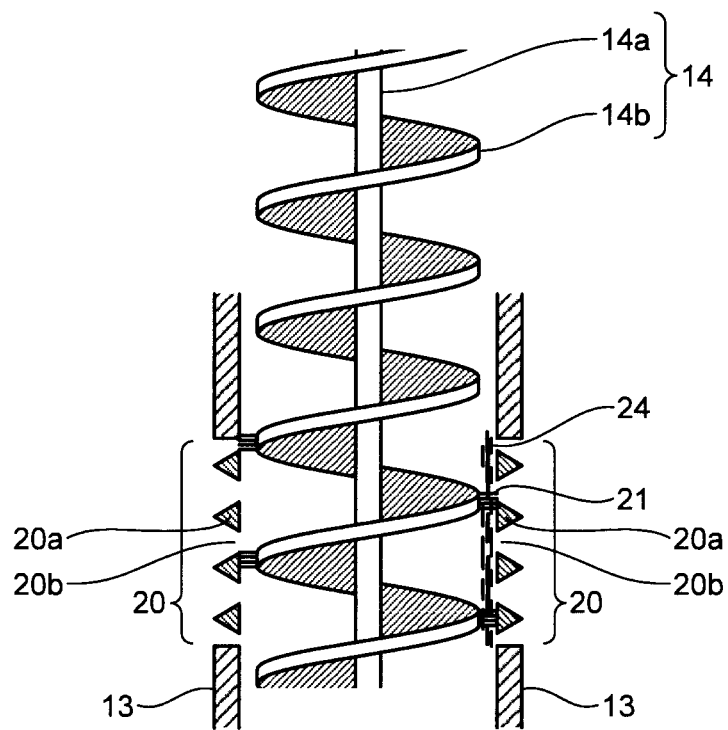
FIG. 2A is a schematic diagram of relevant parts of a solid-liquid separator.

Exemplary embodiments of the present invention will be explained below in detail with reference to the accompanying drawings. The present invention is not limited to the embodiments. In addition, constituent elements in the following embodiments include those that can be easily assumed by persons skilled in the art or that are substantially equivalent. In an embodiment of the present invention, a biomass decomposition apparatus that processes a biomass material is explained by using a hydrothermal decomposition apparatus; however, the present invention is not limited thereto, and same operations can be applied to an apparatus that decomposes a biomass material by adding acid or alkali.

First Embodiment

The biomass decomposition apparatus according to the present invention is explained with reference to the drawings.

FIG. 1 is a schematic diagram of a biomass hydrothermal decomposition apparatus according to a first embodiment. As shown in FIG. 1, a biomass hydrothermal decomposition apparatus 10A according to the first embodiment is a biomass decomposition apparatus that decomposes a biomass material 11 containing cellulose, hemicellulose, and lignin. The biomass decomposition apparatus includes a hydrothermal decomposition unit 17 that transports the fed biomass material 11 from one side (a lower side in the present embodiment) to the other side (an upper side in the present embodiment) by a screw 14 in an apparatus body 13, feeds pressurized hot water 15, which is treat water, from the other side (the upper side in the present embodiment) different from a feed position of the biomass material 11 into the apparatus body 13, hydrothermally decomposes the biomass material 11 while bringing the biomass material 11 into counter contact with the pressurized hot water 15, transfers hot-water soluble fractions into a hot-water effluent 16, which is pressurized hot water to be discharged, and separates a lignin component and a hemicellulose component from the biomass material 11. The biomass decomposition apparatus also includes a biomass discharging unit 19 that discharges a biomass solid 18 from the other side (the upper side in the present embodiment) of the apparatus body 13, and a solid-liquid separator 20 that discharges the hot-water effluent 16 from the one side (the lower side in the present embodiment) of the apparatus body 13. Further, a scraping unit 21 is provided at an end of a flight of the screw 14 positioned within an installation area of the solid-liquid separator 20.

In FIG. 1, reference numeral 12 denotes a biomass feeding unit, reference letter M denotes a motor that drives the screw 14, and reference numeral 23 denotes pressurized nitrogen for keeping a pressure to the inside of the apparatus body 13.

Figure 2B:
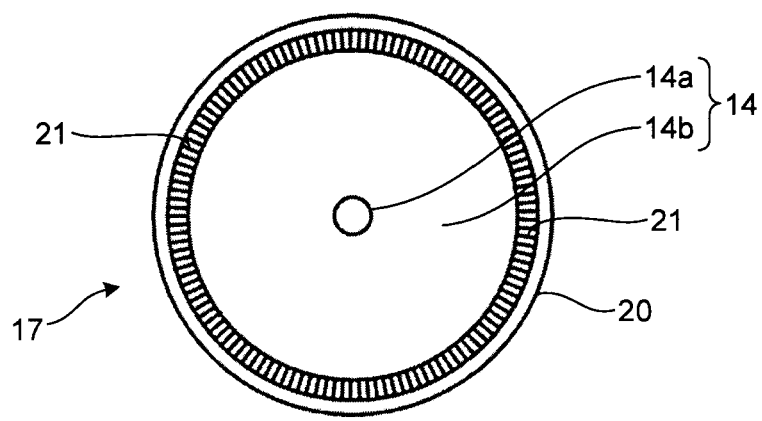
FIG. 2B is a sectional view of the solid-liquid separator.

FIG. 2A is a schematic diagram of relevant parts of the solid-liquid separator, and FIG. 2B is a sectional view thereof.

As shown in FIGS. 2A and 2B, the screw 14 includes a rotation shaft 14a and a spiral flight 14b provided along the rotation shaft 14a, and the scraping unit 21 is provided at the end of the flight 14b. In the present embodiment, the scraping unit 21 is provided continuously at the end of the flight 14b.

Accordingly, a solid content 24 present in the apparatus and accumulated in the solid-liquid separator 20 is scraped off by the scraping unit 21 and transferred upward due to a transporting function of the flight 14b, and is used as a material used for counter contact together with the fed biomass material 11, thereby enabling to efficiently promote hydrothermal decomposition.

As the solid content 24 present in the apparatus to be scraped off by the solid-liquid separator 20, one in which the biomass material 11 or a part of the biomass material 11 is hydrothermally decomposed, the biomass solid 18 and the like can be mentioned.

Figure 3:
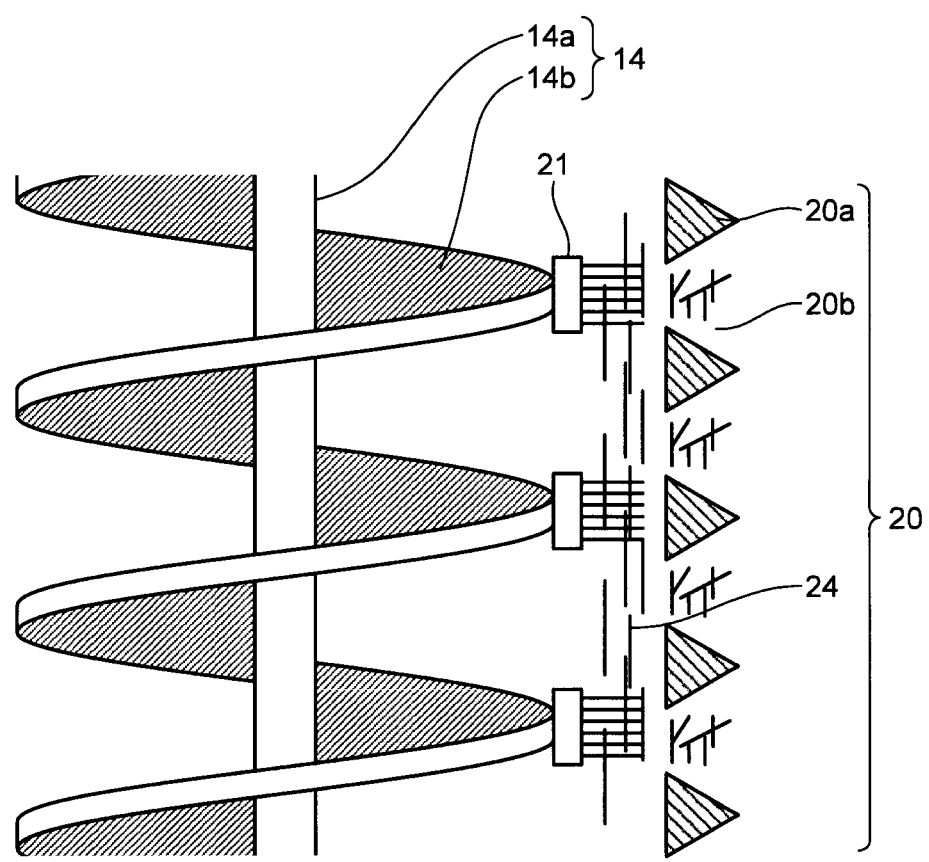
FIG. 3 is a schematic diagram of a solid-liquid separator and a scraping unit.

FIG. 3 is an enlarged view of the solid-liquid separator 20 and the scraping unit 21, and FIGS. 4A to 4D are schematic diagrams of the scraping unit in an undesirable example. In FIGS. 4A to 4D, because right and left are symmetric to the shaft, only the right side is shown.

Figure 4A:
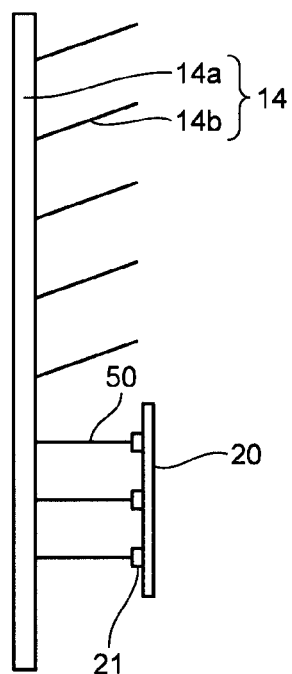
FIG. 4A is a schematic diagram of a solid-liquid separator and a scraping unit according to a comparative example.

As shown in FIG. 4A, for example, when the scraping unit 21 such as a scraper (a brush) is installed via a paddle shaft 50 orthogonal to the rotation shaft 14a, the paddle shaft 50 rotates in the same plane. Therefore, when the solid content 24 present in the apparatus and accumulated on a filter 20a in the solid-liquid separator 20 is scraped off by the scraping unit 21, only the same plane of the solid-liquid separator 20 is scraped and a scraped substance cannot be transported in the same manner as by the screw.

Figure 4B:
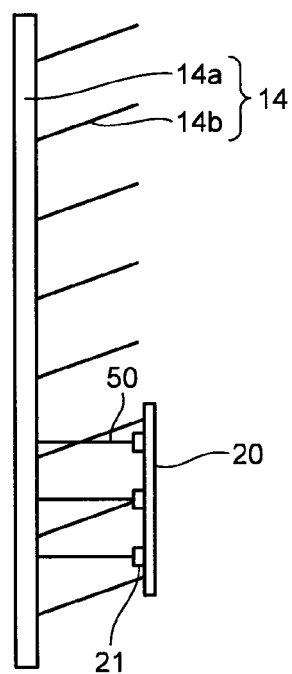
FIG. 4B is a schematic diagram of the solid-liquid separator and the scraping unit according to the comparative example.

As shown in FIG. 4B, even if the flight 14b is installed between the paddle shafts 50 to transport the scraped substance, there is not much difference because only the same plane of the solid-liquid separator 20 can be scraped as in FIG. 4A.

Figure 4C:
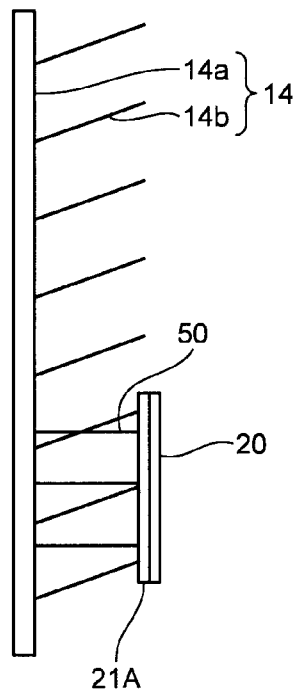
FIG. 4C is a schematic diagram of the solid-liquid separator and the scraping unit according to the comparative example.
Figure 4D:
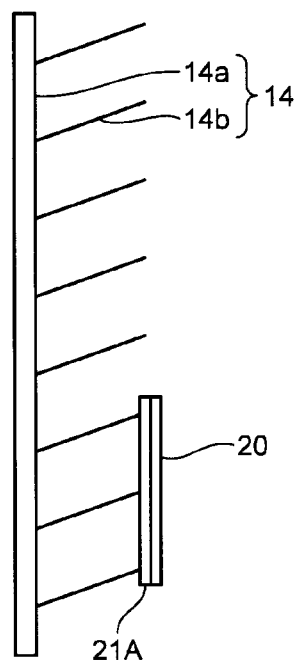
FIG. 4D is a schematic diagram of the solid-liquid separator and the scraping unit according to the comparative example.

As shown in FIG. 4C or 4D, when a scraping unit 21A is installed crosswise (parallel to the rotation shaft 14a), spanning over the ends of the paddle shaft 50 and the ends of the flight 14b, the entire surface of the solid-liquid separator 20 can be scraped. However, because there is a decrease in the frictional force between the solid content and an outer wall (screen surface), which becomes a driving force of transport by the screw 14, the scraped solid content 24 and the like are not efficiently transported by the flight 14b, remain between the flights 14b, and cannot be transported, thereby causing a problem of blockage.

On the other hand, in the present embodiment, as shown in FIG. 3, the scraping unit 21 is provided at the end of the flight 14b, and the tip thereof comes in contact with the surface of the filter 20a. Accordingly, the solid content 24 present in the apparatus is reliably scraped off and transported.

The scraping unit 21 are provided at a plurality of positions or with a predetermined interval on the entire circumference of the flight, so that the solid content 24 in the apparatus can be reliably scraped off from the filter. It is preferable to provide the scraping unit 21 continuously along the flight and spirally, and an installation range thereof is such that a slightly wider range than the solid-liquid separator can be scraped.

Because the scraping unit 21 are continuously provided at a plurality of positions or with a predetermined interval on the entire circumference of the flight, or continuously provided, the entire surface of the solid-liquid separator 20 can be scraped reliably.

Installation of the scraping unit 21 can be appropriately set according to a pitch of the flight 14b or the installation range of the solid-liquid separator.

For example, a brush or a pallet that can scrape off the solid content 24 present in the apparatus and accumulated on the filter 20a can be used as the scraping unit 21.

It is desired that the scraping unit 21 has a brush shape formed by bundling wires. This is because the solid content accumulated on the mesh surface of the filter 20a that performs solid-liquid separation can be scraped off and the solid content accumulated in the mesh can be pushed out or scraped by the scraping unit 21 having a brush shape formed by bundling wires.

It is also desired that one wire constituting the brush has a wire diameter insertable into the gap (mesh) of the filter 20a in the solid-liquid separator 20. By having such a wire diameter, the wire can be inserted into the gap for scraping off the solid content accumulated in the mesh of the filter 20a that performs solid-liquid separation or pushing out the blocked solid content, which is hard to be scraped off.

It is also desired that one wire is formed of a twisted wire formed by twisting thin wires. This is because warpage easily occurs in one independent wire during the operation and scraping action deteriorates. However, by using the twisted wire, warpage hardly occurs.

Further, it is desired that the brush obtained by bundling wires has a width such that the frictional force between a biomass layer and the outer wall (screen surface), which is the driving force of transport by the screw 14, is not reduced.

In this manner, the brush of the scraping unit 21 can include one obtained by simply bundling wires or one obtained by bundling twisted wires. The present invention is not limited thereto so long as the brush can scrape off biomass efficiently. The biomass solid 18 has such a property that biomass having, for example, a fibrous form becomes entangled and accumulates like a layered form. Therefore, when the biomass solid 18 is pressed and removed, removal thereof becomes difficult; however, if the biomass solid 18 advances on the surface so that the biomass solid 18 is scraped off in a transverse direction orthogonal to a laminating direction with respect to sedimentary facies, the solid content 24 present in the apparatus can be easily scraped off.

As shown in FIG. 2A, the solid-liquid separator 20 includes the filter 20a that separates the solid content 24 present in the apparatus and a hot-water effluent from each other and a slit 20b for discharging the separated hot-water effluent 16 to outside.

The solid-liquid separator 20 is formed over the entire circumference of the apparatus body 13; however, when the hot-water effluent 16 can be efficiently discharged, the solid-liquid separator 20 need not be formed over the entire circumference thereof.

The slits 20b for discharging the hot-water effluent 16 formed on the filter 20a can be horizontal stripes or vertical stripes.

Figure 5:
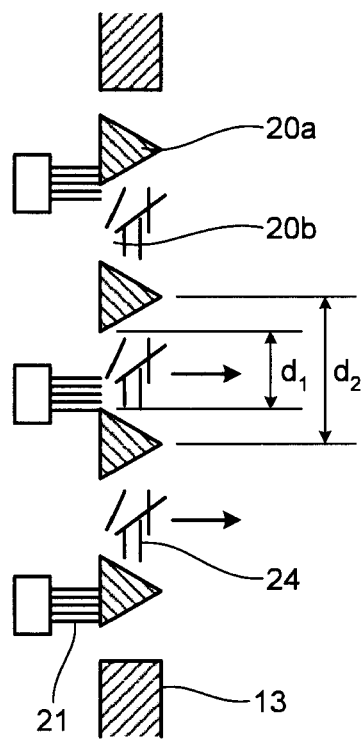
FIG. 5 is a schematic diagram of a filter in a solid-liquid separator.

FIG. 5 is a schematic diagram of the filter in the solid-liquid separator.

As shown in FIG. 5, an aperture shape of the filter 20a in the solid-liquid separator 20 expands from a width d1 on an inlet side toward a width d2 on an outlet side.

As a result, even if the solid content 24 present in the apparatus becomes blocked in the slits 20b formed between the filters 20a, the solid content 24 present in the apparatus is easily taken out to outside due to a push-out action such that the tips of the brush, which is the scraping unit 21, enter into the slits 20b.

Because solid-liquid separation is performed in the apparatus body 13, solid-liquid separation can be performed in a state with temperature in the apparatus body 13 being high, differently from a case that an effluent is discharged to outside in a solid-liquid mixed state as in conventional proposals.

As a result, the liquid viscosity of the hot-water effluent 16 becomes low, thereby facilitating solid-liquid separation.

Further, differently from the case that the effluent is discharged to outside in the solid-liquid mixed state, precipitates are not generated due to temperature drop. Therefore, a pressure loss in the filter 20a is small, and a load due to precipitates is hardly generated, thereby enabling to reduce the size of the filter 20a.

Further, differently from the case that that effluent is discharged to outside in the solid-liquid mixed state, there is only a little loss in the precipitates due to temperature drop. Therefore, efficient hydrothermal decomposition reaction can be performed, and a material loss of a saccharification material starting from the hot-water effluent 16 becomes small.

Figure 6:
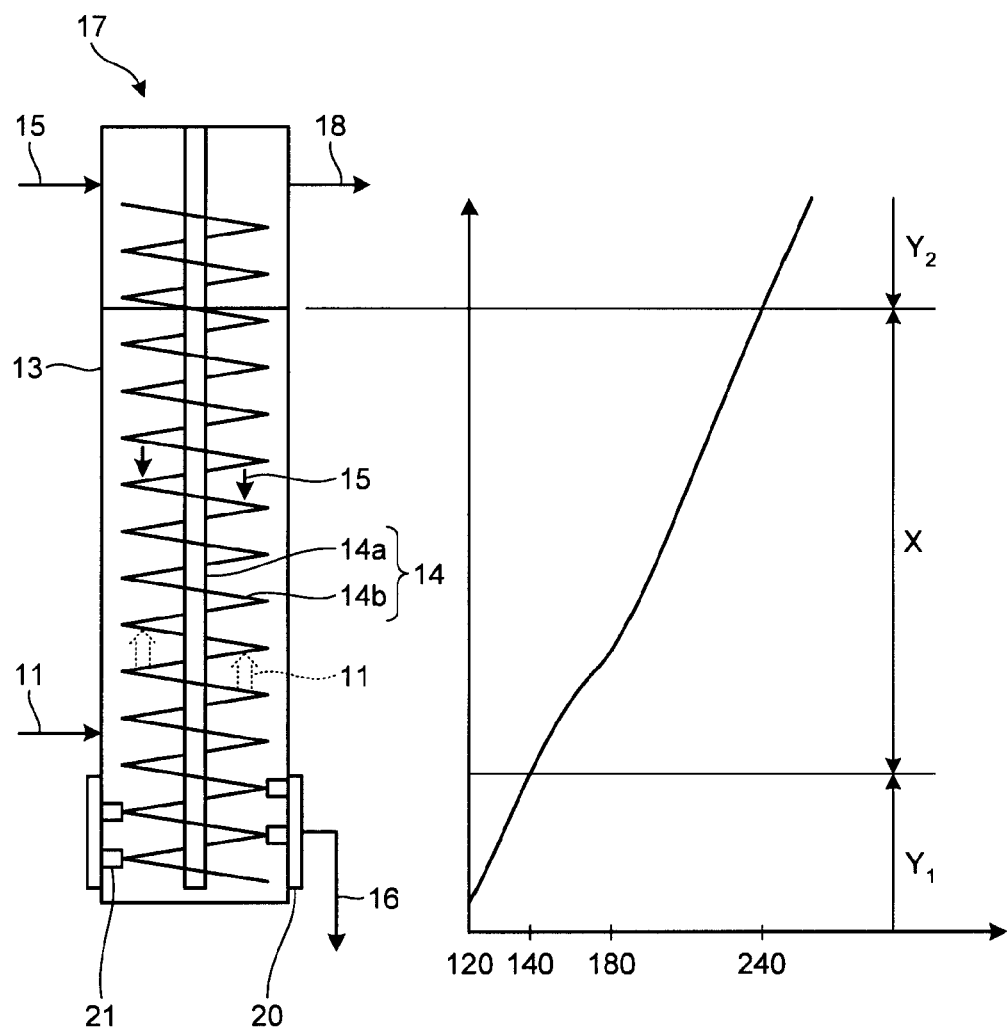
FIG. 6 is a pattern diagram of a vertical hydrothermal decomposition apparatus that hydrothermally decomposes biomass by hot water and a temperature distribution diagram thereof.

An outline of hydrothermal decomposition of the biomass material 11 by the hydrothermal decomposition unit 17 is explained next. FIG. 6 is a pattern diagram of a vertical hydrothermal decomposition apparatus that hydrothermally decomposes biomass by hot water and a temperature distribution diagram thereof.

The hydrothermal decomposition unit 17 feeds the biomass material 11 and the pressurized hot water 15 to come into counter contact with each other, and causes hydrothermal reaction between the biomass material 11 and the pressurized hot water 15 by internal heat exchange. In FIG. 6, a non-counter contact zone (a low temperature side) $Y_1$, a counter contact zone X, and a non-counter contact zone (a high temperature side) $Y_2$ are shown, and in the non-counter contact zone (a low temperature side) $Y_1$, these are rapidly cooled to 140° C. or lower.

As shown in FIG. 6, the vertical hydrothermal decomposition apparatus feeds the biomass material (a solid form) 11 from the lower side into the apparatus body 13, transfers the biomass material upward by the screw 14 provided therein, and discharges the biomass solid (a hot-water insoluble) 18 from the upper side to outside through a solid-content discharging unit (not shown).

On the other hand, because the solid-liquid separator 20, which is a hot-water discharge unit, is on the lower side than a feed position of the biomass material 11, the solid-liquid separator 20 does not disturb counter contact between the pressurized hot water 15 and the biomass material 11. However, if the solid content is accumulated on the filter 20a in the solid-liquid separator 20 due to the flow of the pressurized hot water 15, accumulation is suppressed by scraping off the solid content by the scraping unit 21, thereby performing solid-liquid separation reliably.

The scraped-off solid content 24 present in the apparatus is transferred (lifted) by a transporting function of the flight 14b of the screw 14. As a result, the solid content 24 is returned to the counter contact zone X, and the biomass material 11 in the solid content 24 present in the apparatus is used as a material for hydrothermal decomposition again, thereby promoting efficient hydrothermal decomposition.

The biomass to be fed to the hydrothermal decomposition unit 17 is not particularly limited, and is organisms incorporated in a substance circulatory system of the global biosphere or accumulation of organic matters derived from the organisms (see JIS K 3600 1258). In the present invention, it is particularly preferable to use cellulose resources such as broad-leaved plants and herbs, agricultural waste, or food waste.

The particle diameter of the biomass material 11 is not particularly limited; however, it is desired to mill the biomass material 11 into a small particle size of 5 millimeters or less.

In the present embodiment, before feeding biomass, for example, a mill can be used as a pre-processing unit to perform pre-processing. Further, biomass can be cleaned by a cleaning device.

For example, when chaff is used as the biomass material 11, chaff can be fed as it is to the biomass feeding unit 12 without milling.

It is desired that the reaction temperature in the hydrothermal decomposition unit 17 is in a range from 180° C. to 240° C., and more preferably from 200° C. to 230° C.

This is because hydrothermal decomposition rate is low at a temperature of 180° C. or lower, and a long decomposing time is required. Therefore, this leads to an increase in size of the apparatus, and it is not preferable. On the other hand, at a temperature exceeding 240° C., the decomposition rate becomes excessive, transfer of the cellulose component from a solid phase to a liquid phase increases, and excessive decomposition of hemicellulose sugar is promoted, which is not preferable.

The hemicellulose component dissolves at about 140° C., cellulose dissolves at about 230° C., and the lignin component dissolves at about 140° C. However, it is desired that cellulose is left on the solid content side, and the temperature is set to a range from 180° C. to 240° C., at which the hemicellulose component and the lignin component can maintain sufficient decomposition rate.

As a reaction pressure, it is desired that a pressure higher by 0.1 to 0.5 megapascal is applied to a saturated vapor pressure of water at respective temperatures of the reaction temperature (180° C. to 240° C.) of the apparatus body 13.

It is also desired that a reaction time is equal to or shorter than 20 minutes, and preferably, from 3 to 10 minutes. This is because if the reaction time is too long, the rate of excessive decomposition product increases, which is not preferable.

As the biomass feeding unit 12 that feeds biomass under a normal pressure to under an increased pressure, for example, means such as a screw, piston pump, or slurry pump can be mentioned.

In the present embodiment, the hydrothermal decomposition apparatus is a vertical apparatus. However, the present invention is not limited thereto, and for example, a gradient-type hydrothermal decomposition apparatus can be used, so long as the apparatus brings hot water into counter contact with the biomass material from one side to decompose the biomass material, while transferring the biomass material from the other side to the one side.

The reason why the hydrothermal decomposition apparatus is the gradient type or vertical type is that gas generated in the hydrothermal decomposition reaction and gas brought into the material can quickly escape from above, which is preferable. Further, because the decomposition product is extracted by the pressurized hot water 15, concentration of the extracted product increases from the upper side toward the lower side, which is preferable in view of the extraction efficiency.

As described above, according to the present embodiment, the solid content 24 present in the apparatus and accumulated in the solid-liquid separator 20 is scraped off and removed by the scraping unit 21 provided at the end of the flight 14b of the screw 14 to prevent blockage. The removed solid content 24 is lifted due to a transporting function of the flight 14b. As a result, the biomass material 11 in the solid content 24 and the biomass material 11 being decomposed are used as a material for counter contact in the apparatus body 13, thereby promoting efficient hydrothermal decomposition.

In the present embodiment, the hydrothermal decomposition apparatus is explained as the biomass decomposition apparatus that decomposes biomass. However, the present invention is not limited thereto, and blockage in the solid-liquid separator can be efficiently suppressed even by, for example, an alkaline decomposition processing device (for example, decomposition by using sodium hydroxide, lime hydrate, or ammonia) or an acid decomposition processing device (decomposition by using diluted sulfuric acid), so long as it brings treat water into counter contact with the biomass material from one side to decompose the biomass material, while transferring the biomass material from the other side to the one side.

Second Embodiment

A biomass hydrothermal decomposition apparatus according to another embodiment of the present invention is explained next with reference to FIG. 7. Elements identical to those in the biomass hydrothermal decomposition apparatus according to the first embodiment are denoted by like reference letters or numerals and explanations thereof will be omitted.

Figure 7:
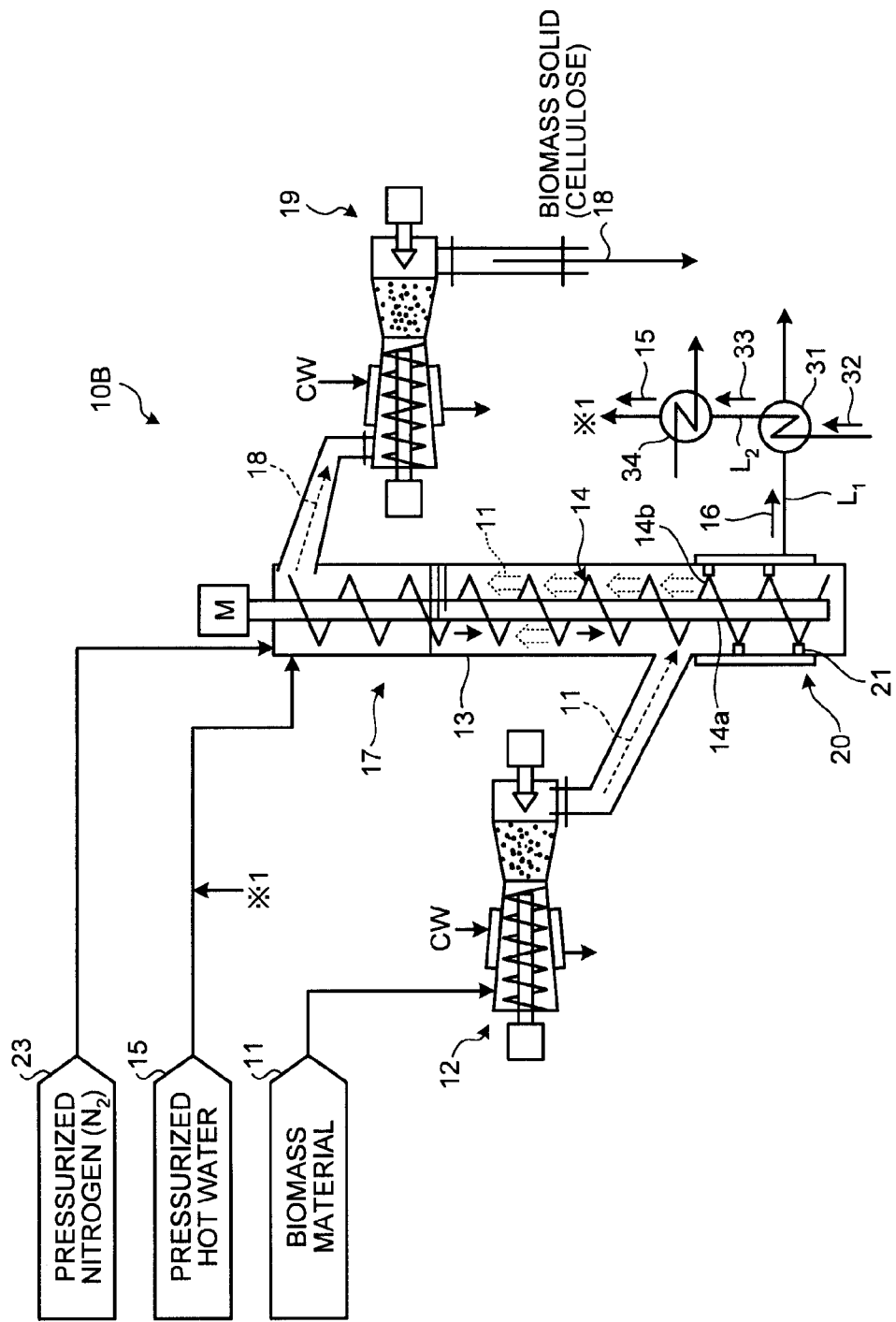
FIG. 7 is a schematic diagram of a biomass hydrothermal decomposition apparatus according to a second embodiment of the present invention.

FIG. 7 is a schematic diagram of a biomass hydrothermal decomposition apparatus according to a second embodiment.

As shown in FIG. 7, a biomass hydrothermal decomposition apparatus 10B includes a heat exchanger 31 provided in an discharge line $L_1$ of the hot-water effluent 16 discharged from the solid-liquid separator 20, in the biomass hydrothermal decomposition apparatus 10A according to the first embodiment, to cool the hot-water effluent 16 by water 32. A heater 34 is provided in a feed line $L_2$ to heat heat-exchanged hot water 33 under an increased pressure, which is then fed to the hydrothermal decomposition unit 17 as the pressurized hot water 15 and reused.

Third Embodiment

A biomass hydrothermal decomposition apparatus according to another embodiment of the present invention is explained next with reference to FIG. 8. Elements identical to those in the biomass hydrothermal decomposition apparatus according to the first embodiment are denoted by like reference letters or numerals and explanations thereof will be omitted.

Figure 8:
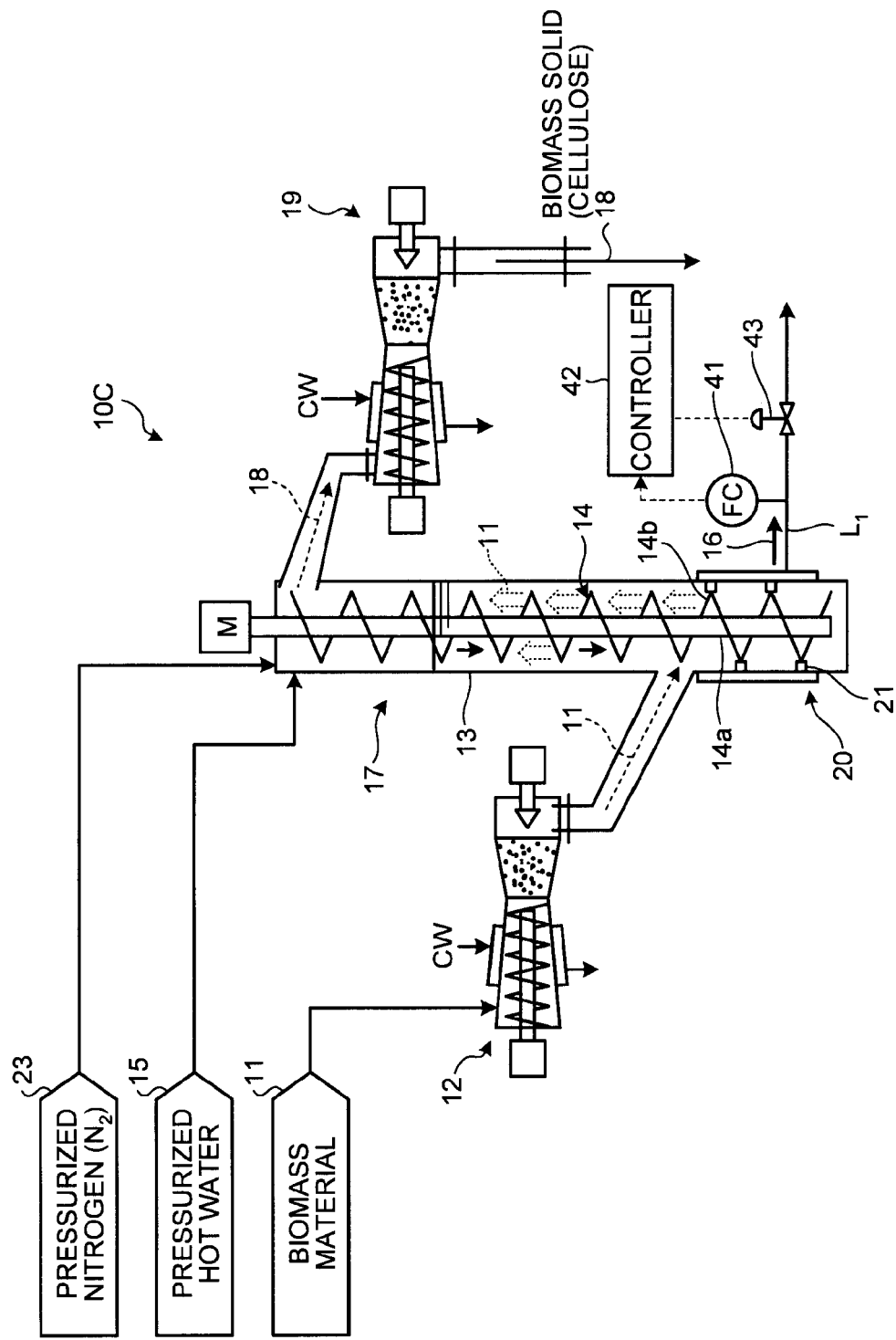
FIG. 8 is a schematic diagram of a biomass hydrothermal decomposition apparatus according to a third embodiment of the present invention.

FIG. 8 is a schematic diagram of a biomass hydrothermal decomposition apparatus according to a third embodiment.

As shown in FIG. 8, a biomass hydrothermal decomposition apparatus 10C includes a flowmeter 41 provided in the discharge line $L_1$ of the hot-water effluent 16, in the biomass hydrothermal decomposition apparatus 10A in the first embodiment, to control an aperture of a valve 43 by a controller 42, so that an discharge flow rate becomes constant.

As a result, the discharge flow rate is maintained constant at all times, and the solid content 24 present in the apparatus and accumulated on the filter 20a and the scraped amount by the scraping unit 21 are stabilized at all times (a differential pressure of the filter is maintained constant), thereby enabling to stabilize the operation of a reaction apparatus.

On the other hand, liquid level control of the hydrothermal decomposition unit 17 can be also performed; however, it is desired to perform flow rate control of the effluent, in view of stability.

Fourth Embodiment

A production system of alcohol, which is an organic material, using a biomass material according to a fourth embodiment of the present invention is explained with reference to FIG. 9.

Figure 9:
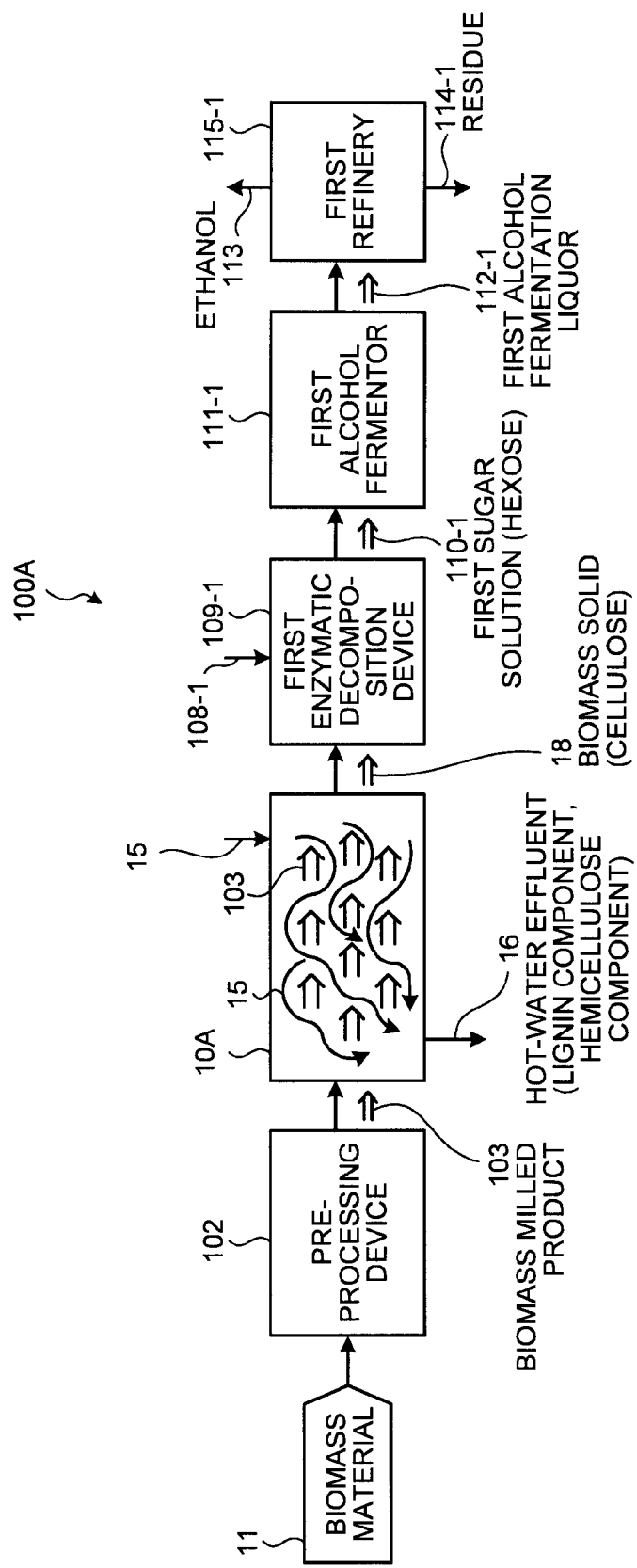
FIG. 9 is a conceptual diagram of a production system of an organic material using a biomass material according to a fourth embodiment of the present invention.

FIG. 9 is a conceptual diagram of a production system of an organic material using the biomass material according to the fourth embodiment.

As shown in FIG. 9, an alcohol production system 100A using the biomass material according to the present embodiment includes a pre-processing device 102 that performs, for example, milling of the biomass material 11, the hydrothermal decomposition apparatus 10A shown in FIG. 1 that performs hydrothermal decomposition of the biomass material, while bringing a preprocessed biomass milled product 103 into counter contact with the pressurized hot water 15, to transfer the lignin component and the hemicellulose component into the pressurized hot water 15, thereby separating the lignin component and the hemicellulose component from a biomass solid, a first enzymatic decomposition device 109-1 that processes cellulose in the biomass solid 18 discharged from the hydrothermal decomposition apparatus 10A with enzyme to decompose cellulose into a sugar solution containing hexose by a first enzyme (cellulase) 108-1, a first alcohol fermentor 111-1 that produces alcohol (ethanol in the present embodiment) by fermentative treatment by using a first sugar solution (hexose) 110-1 obtained by the first enzymatic decomposition device 109-1, and a first refinery 115-1 that refines a first alcohol fermentation liquor 112-1 to separate the first alcohol fermentation liquor 112-1 into ethanol 113, which is a desired product, and a residue 114-1.

According to the present invention, in the biomass hydrothermal decomposition apparatus 10A as shown in FIG. 1, the lignin component and the hemicellulose component are transferred into the pressurized hot water 15 on the liquid side by adopting counter contact, so that cellulose remains in the biomass solid 18 on the solid side, thereby acquiring the first sugar solution (hexose) 110-1 by the first enzymatic decomposition device 109-1 for enzymic saccharification.

Accordingly, a fermenting process according to hexose (fermentation according to an end product: in the present embodiment, the ethanol 113 is obtained due to fermentation by using the first alcohol fermentor 111-1) can be established.

In the present embodiment, ethanol of alcohol is exemplified as the product to be obtained by the fermentative treatment. However, the present invention is not limited thereto, and petroleum substitutes, which become chemical product raw materials, or amino acid, which becomes a food/feed material other than alcohol can be obtained by the fermentor.

Further, various organic materials (for example, alcohol, petroleum substitutes, or amino acid) such as LPG, automotive fuel, aircraft jet fuel, kerosene petroleum, diesel oil, various heavy oils, fuel gas, naphtha, ethylene glycol as naphtha decomposition product, lactic acid, alcohol (ethanol and the like), amine, alcohol ethoxylate, vinyl chloride polymer, alkyl aluminum, PVA, vinyl acetate emulsion, polystyrene, polyethylene, polypropylene, polycarbonate, MMA resin, nylon, and polyester can be efficiently produced from a sugar solution. Therefore, the sugar solution derived from biomass can be efficiently used as substitutes of chemical products derived from crude oil, which is a depleting fuel, and as a raw material for producing the substitutes.

Fifth Embodiment

A production system of alcohol, which is an organic material, using a biomass material according to a fifth embodiment of the present invention is explained with reference to FIG. 10.

Figure 10:
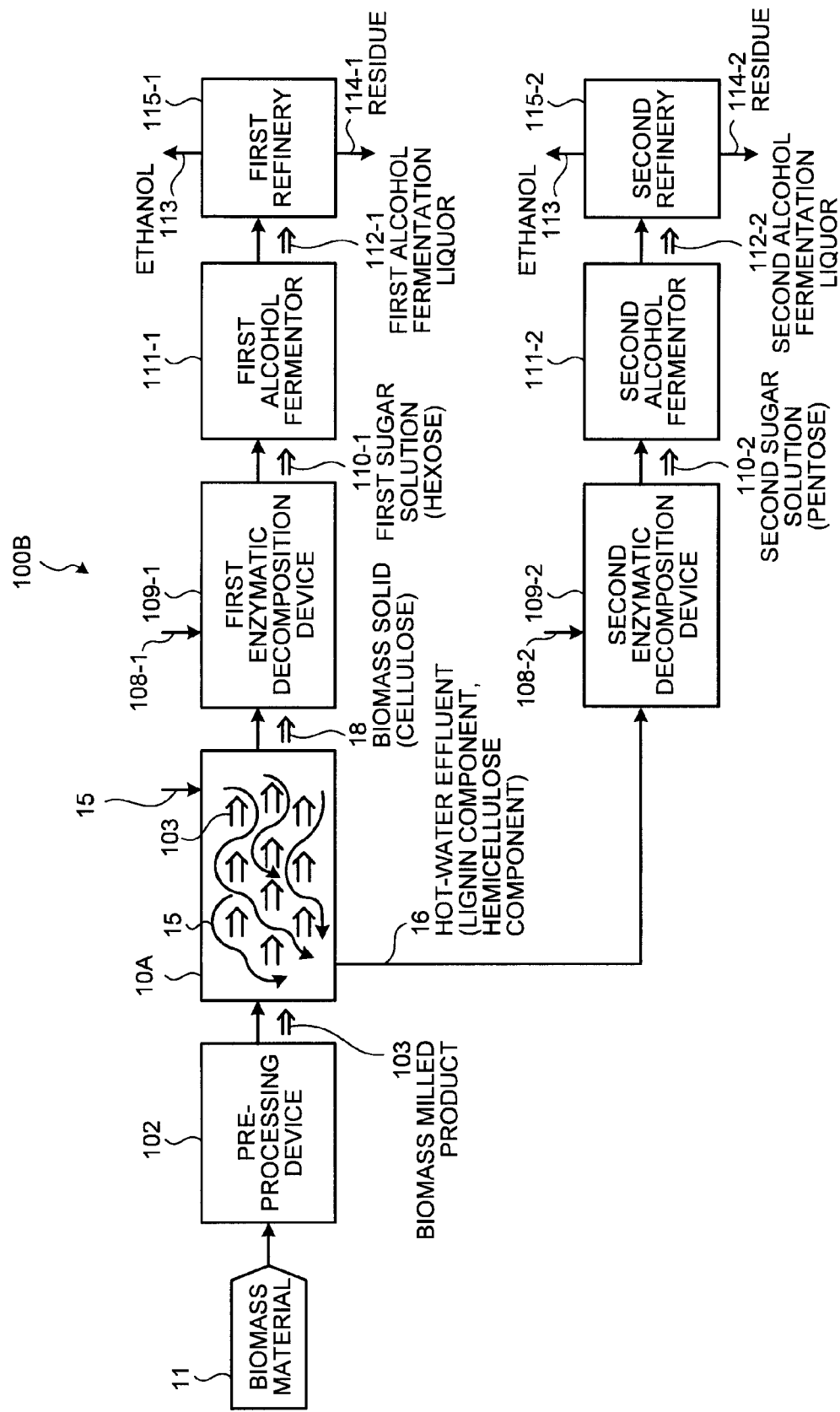
FIG. 10 is a conceptual diagram of an alcohol production system of an organic material using a biomass material according to a fifth embodiment of the present invention.

FIG. 10 is a conceptual diagram of a production system of alcohol, which is an organic material, using the biomass material according to the fifth embodiment.

As shown in FIG. 10, an alcohol production system 100B using the biomass material according to the present embodiment includes a second enzymatic decomposition device 109-2 that processes a hemicellulose component transferred into the hot-water effluent 16 discharged from the hydrothermal decomposition apparatus 10A with enzyme, to decompose the hemicellulose component into a second sugar solution 110-2 containing pentose, in the alcohol production system 100A shown in FIG. 9.

Two enzymatic decomposition devices, two alcohol fermentors, and two refineries (the first and second enzymatic decomposition devices 109-1 and 109-2, the first alcohol fermentor 111-1 and a second alcohol fermentor 111-2, and the first refinery 115-1 and a second refinery 115-2) are provided separately. The ethanol 113 is obtained by performing an enzymatic decomposition process, an alcohol fermentation process, and a refining process according to the first sugar solution (hexose) 110-1 and the second sugar solution (pentose) 110-2.

In the present embodiment, after a second alcohol fermentation liquor 112-2 is obtained by the fermentation process performed by the second alcohol fermentor 111-2 by using the second sugar solution (pentose) 110-2 obtained by the second enzymatic decomposition device 109-2 using the second enzyme 108-2, the ethanol 113 can be produced by the second refinery 115-2. Reference numeral 114-2 denotes a residue.

Hot-water effluent is not always processed in separate systems, and various changes can be made such that, for example, a process after the enzymatic decomposition device is communalized, a process after the alcohol fermentor is communalized, or a process after the refinery is communalized.

Figure 11:
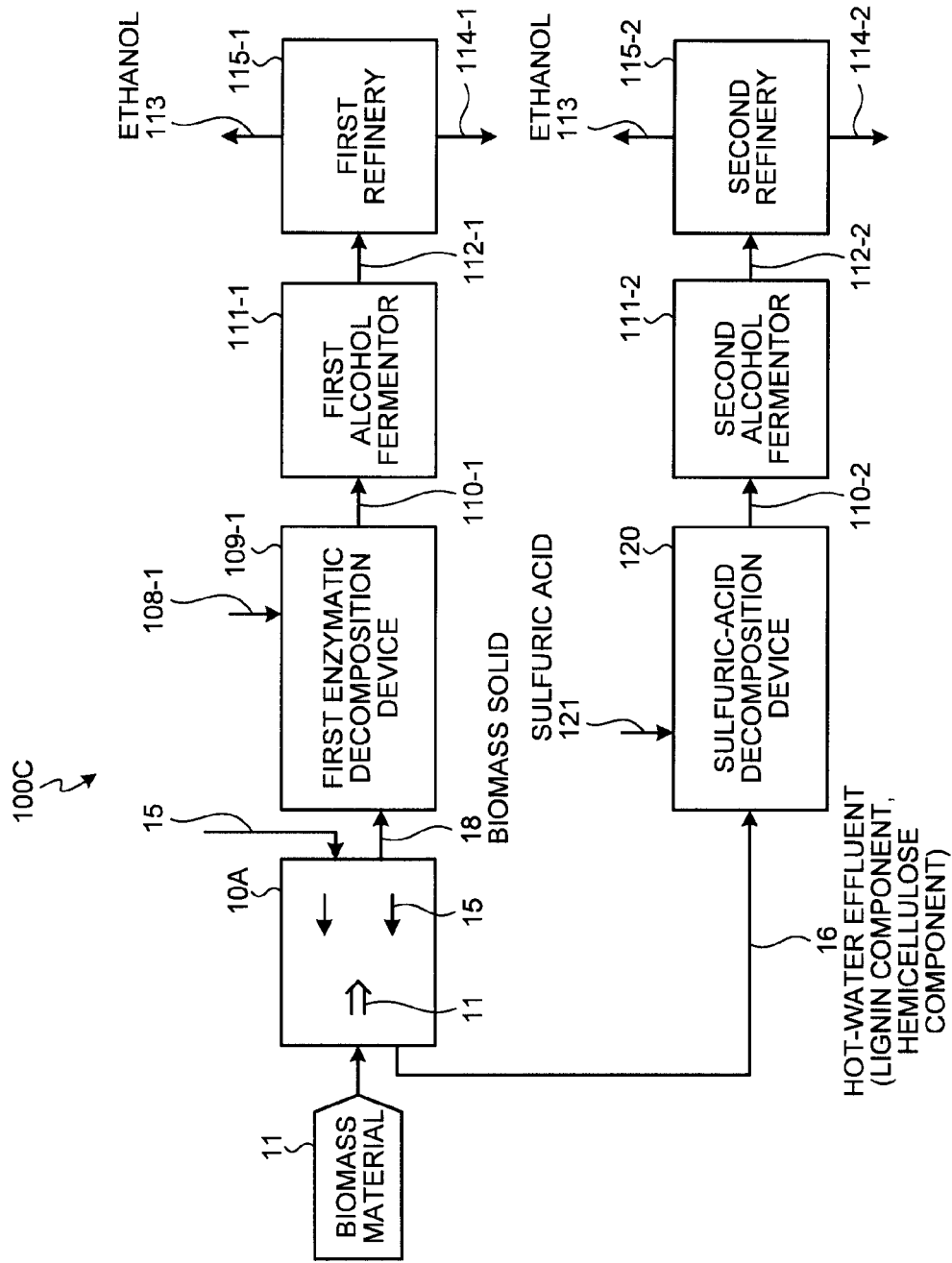
FIG. 11 is a conceptual diagram of an alcohol production system of an organic material using a biomass material according to a modification of the fifth embodiment.

FIG. 11 is a conceptual diagram of a production system of alcohol, which is an organic material, using a biomass material according to a modification of the present embodiment.

As shown in FIG. 11, in the alcohol production system 100A shown in FIG. 9, an alcohol production system 100C according to the present embodiment includes a sulfuric-acid decomposition device 120 that discharges the pressurized hot water 15, into which the lignin component and the hemicellulose component are transferred, to outside as the hot-water effluent 16, feeds sulfuric acid 121 to the hot-water effluent 16, and decomposes the hemicellulose component in the hot-water effluent 16 with sulfuric acid to decompose the hemicellulose component into the second sugar solution 110-2 containing pentose, the second alcohol fermentor 111-2 that produces alcohol (ethanol in the present embodiment) by the fermentative treatment by using the obtained second sugar solution (pentose) 110-2, and the second refinery 115-2 that refines the second alcohol fermentation liquor 112-2 to separate the second alcohol fermentation liquor 112-2 into the ethanol 113, which is a desired product, and a second residue 114-2.

In the present embodiment, the ethanol 113 can be produced by the fermentative treatment by using the second sugar solution (pentose) 110-2 obtained by the sulfuric-acid decomposition device 120.

Decomposition conditions for the sulfuric-acid decomposition device in the present invention are such that concentration of sulfuric acid is 0.1% to 5% by weight, preferably, 1% to 4% by weight, decomposition temperature is 100° C. to 140° C., preferably about 120° C., and a decomposition time is for 30 minutes to 3 hours, preferably, about 1 hour. This is because, if the decomposition conditions are outside these ranges, favorable decomposition of hemicellulose cannot be realized.

Conventionally, when the biomass material is directly decomposed with sulfuric acid, the decomposition process is performed at a temperature as high as about 180° C. for about 10 minutes, by using 1% by weight of sulfuric acid. However, because sulfuric acid acts as an inhibitor at the time of enzymic saccharification of cellulose on a downstream side, the yield of hexose decreases.

On the other hand, in the present invention, in the biomass hydrothermal decomposition apparatus 10A, the cellulose component is caused to remain in the biomass solid 18 beforehand, to process the hot-water effluent 16 containing the hemicellulose component transferred to the pressurized hot water 15 side with sulfuric acid under a low-temperature condition. Therefore, the process of sulfuric acid facilities can be simplified, and usage of sulfuric acid can be considerably suppressed (from 0.6 to 0.9 times the conventional usage of sulfuric acid). As a result, the amount of disposal (gypsum treatment) of sulfuric acid is reduced, thereby enabling to reduce the facility size for recovering and separating sulfuric acid and downsize the facilities.

Because decomposition using sulfuric acid can be performed at a temperature as low as 140° C. or lower, any conventional corrosion-resistant facilities for high temperature (180° C.) is not required, thereby enabling to reduce the cost of the facilities.

According to the present invention, in the biomass hydrothermal decomposition apparatus 10A (10B, 10C), by adopting counter contact, cellulose remains in the biomass solid 18 on the solid side, and the first enzymatic decomposition device 109-1 for enzymic saccharification obtains the first sugar solution (hexose) 110-1, and in the pressurized hot water 15 on the liquid side, the hemicellulose component dissolved in the pressurized hot water 15 is separated as the hot-water effluent 16. The second enzymatic decomposition device 109-2 for enzymic saccharification or the sulfuric-acid decomposition device 120 obtains the second sugar solution (pentose) separately. Therefore, the both sugar solutions can be efficiently separated and saccharized, respectively. The fermentation process according to hexose and pentose (fermentation according to the end product: for example, ethanol fermentation) can be established.

As described above, by adopting counter contact in the biomass hydrothermal decomposition apparatus 10A, a side reaction product, which becomes an inhibitor in the enzymic saccharification reaction for obtaining hexose, and the lignin component soluble in pressurized hot water are transferred to the pressurized hot water 15 side. Therefore, the cellulose-based biomass solid 18 can be obtained, thereby improving the saccharification yield of hexose in the saccharification reaction thereafter.

On the other hand, the hemicellulose component contained in the separated hot-water effluent 16 is saccharized in the second enzymatic decomposition device 109-2, thereby enabling to obtain the sugar solution containing pentose.

By using a suitable yeast or the like suitable for hexose and pentose, respectively, the ethanol 113 can be efficiently and individually obtained by fermentation.

As described above, according to the present invention, a production system of an organic material using a biomass material that separates cellulose-based component and hemicellulose component transferred to pressurized hot water, suppresses excessive decomposition of hemicellulose, to enable efficient production of the sugar solutions (a hexose solution and a pentose solution) suitable for respective components, and can efficiently produce various organic materials (for example, alcohol, petroleum substitutes, or amino acid) from the sugar solution can be provided.

INDUSTRIAL APPLICABILITY

As described above, according to the present invention, the biomass solid accumulated in the solid-liquid separator is scraped off by the biomass hydrothermal decomposition apparatus and the method thereof so as to prevent blockage, thereby enabling efficient solid-liquid separation. Further, a sugar solution is produced by using these solid-liquid separation products, and various organic materials (for example, alcohol, petroleum substitutes, or amino acid) can be efficiently produced from the sugar solution.

REFERENCE SIGNS LIST 10A to 10c biomass hydrothermal decomposition apparatus
11 biomass material
12 biomass feeding unit
13 apparatus body
14 screw
15 pressurized hot water
16 hot-water effluent
17 hydrothermal decomposition unit
18 biomass solid
19 biomass discharging unit
20 solid-liquid separator
21 scraping unit
24 solid content present in apparatus

The invention claimed is:

1. A biomass decomposition apparatus that decomposes a biomass material containing cellulose, hemicellulose, and lignin, the apparatus comprising:
a biomass feeding unit that feeds a biomass material;
a vertical decomposition unit that decomposes the biomass material while bringing the biomass material into counter contact with treat water, transfers soluble fractions into an effluent, which is treat water to be discharged, and separates a lignin component and a hemicellulose component from the biomass material so as to produce a biomass solid, the decomposition unit including:
an inlet for receiving biomass material fed by the biomass feeding unit;
an outlet provided above the inlet, for discharging the biomass solid;
a screw including a rotation shaft and a spiral flight, for transporting the biomass material from the inlet to the outlet, the rotation shaft being provided in a longitudinal direction of the vertical decomposition unit; and
a treat water inlet for supplying the treat water;
a biomass discharging unit that discharges the biomass solid from the outlet; and
a solid-liquid separator that is provided below the inlet and discharges the effluent, wherein
a scraping unit for contacting the solid-liquid separator so as to scrape the biomass material is provided on an end of the spiral flight of the screw, the scraping unit being provided at a position associated with the solid-liquid separator, and
the solid-liquid separator includes a filter provided with a plurality of slits which are horizontal stripes vertical to the rotation shaft and each of the slits has an entrance width smaller than an exit width.

2. The biomass decomposition apparatus according to claim 1, wherein the scraping unit abuts against a surface of the solid-liquid separator.

3. The biomass decomposition apparatus according to claim 1, wherein the scraping unit is provided at a plurality of positions over an entire circumference of a flight.

4. The biomass decomposition apparatus according to claim 1, wherein the scraping unit has a brush shape formed by bundling wires.

5. The biomass decomposition apparatus according to claim 1, wherein the solid-liquid separator is a filter.

6. The biomass decomposition apparatus according to claim 4, wherein the solid-liquid separator includes filters and slits and each one of the wires has a wire diameter insertable into a gap between the slits of the solid-liquid separator.

7. The biomass decomposition apparatus according to claim 4, wherein each one of the wires is formed of a twisted wire formed by twisting thin wires.

8. The biomass decomposition apparatus according to claim 1, wherein the solid-liquid separator is formed over an entire circumference of an apparatus body.

9. The biomass decomposition apparatus according to claim 5, wherein an aperture shape of a filter in the solid-liquid separator expands from an inlet side toward an outlet side.

10. The biomass decomposition apparatus according to claim 1, further comprising:
under an increased pressure, a heater for heating water that has been heat-exchanged by the heat exchanger so as to obtain pressurized hot water; and
a pressurized hot-water line for feeding the pressurized hot water to the decomposition apparatus.

11. The biomass decomposition apparatus according to claim 1, wherein a flowmeter is provided in a discharge line of the effluent, and a controller controls a flow rate so that an discharge flow rate becomes constant.

12. The biomass decomposition apparatus according to claim 1, wherein a reaction temperature in the decomposition unit is in a range from 180° C. to 240° C.

13. The biomass decomposition apparatus according to claim 12, wherein as a reaction temperature in the decomposition unit, a pressure higher by 0.1 to 0.5 megapascal is applied to a saturated vapor pressure of water at respective temperatures of the reaction temperature.

14. The biomass decomposition apparatus according to claim 1, wherein a reaction time is equal to or shorter than 20 minutes.

15. A biomass decomposition method according to claim 1, comprising:
feeding a biomass material containing cellulose, hemicellulose, and lignin;
decomposing the biomass material with treat water in the decomposition unit;
dissolving a lignin component and a hemicellulose component in the treat water; and
thereafter, separating a solid content accumulated in the solid-liquid separator into solid and liquid by scraping off a solid content by the scraping unit when an effluent is discharged from the decomposition unit.

16. A sugar-solution production system using a biomass material, comprising:
the biomass decomposition apparatus according to claim 1; and
an enzymatic decomposition device that processes at least one of cellulose in a biomass solid discharged from the biomass decomposition apparatus and a hemicellulose component in an effluent with enzyme into a sugar solution containing at least one of hexose and pentose.

17. The sugar-solution production system using a biomass material according to claim 16, comprising a sulfuric-acid decomposition device that decomposes the hemicellulose component in the effluent discharged from the biomass decomposition apparatus with sulfuric acid into a sugar solution containing pentose.

* * * * *